United States Patent
Stewart et al.

(10) Patent No.: US 11,033,329 B2
(45) Date of Patent: Jun. 15, 2021

(54) TIMED ENERGY DELIVERY

(71) Applicant: Medtronic Ablation Frontiers LLC, Minneapolis, MN (US)

(72) Inventors: Mark T. Stewart, Lino Lakes, MN (US); Catherine R. Condie, Shoreview, MN (US); Jay L. Kelley, Encinitas, CA (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 197 days.

(21) Appl. No.: 16/359,278

(22) Filed: Mar. 20, 2019

(65) Prior Publication Data

US 2019/0216525 A1 Jul. 18, 2019

Related U.S. Application Data

(62) Division of application No. 14/664,269, filed on Mar. 20, 2015, now Pat. No. 10,271,893.

(Continued)

(51) Int. Cl.
*A61B 18/12* (2006.01)
*A61B 18/14* (2006.01)
(Continued)

(52) U.S. Cl.
CPC ...... *A61B 18/1492* (2013.01); *A61B 18/1206* (2013.01); *A61B 2018/00351* (2013.01);
(Continued)

(58) Field of Classification Search
CPC ............ A61B 18/492; A61B 2090/065; A61B 18/1206; A61B 2018/00351;
(Continued)

(56) References Cited

U.S. PATENT DOCUMENTS 7,653,438 B2  1/2010 Deem et al.
7,937,143 B2  5/2011 Demarais et al.
(Continued)

FOREIGN PATENT DOCUMENTS

CN  103781433 A  5/2014
EP  0189329 A2  7/1986
(Continued)

OTHER PUBLICATIONS

English Translation of China National Intellectual Property Administration, Notice on the First Office Action and Search Report, for corresponding International Application No. 201580068265.8, dated Jan. 22, 2019, 10 pages.

(Continued)

*Primary Examiner* — Erin M Piateski
(74) *Attorney, Agent, or Firm* — Christopher & Weisberg, P.A.

(57) ABSTRACT

A method and system for mapping tissue and producing lesions for the treatment of cardiac arrhythmias in a non-thermal and optimal manner, minimizing the amount of energy required to selectively stun or ablate the target tissues. Energy may be delivered only at the moment(s) of best device position and proximity of an electrode to target tissue, and only during a time in the cardiac cycle determined to be optimal for reversible or irreversible effects. A method may include determining timing of the cardiac cycle and an optimal time within the cardiac cycle for energy delivery, evaluating proximity between at least one energy delivery electrode and the target tissue, and delivering pulsed field energy from the at least one energy delivery electrode to the target tissue when, during the optimal time for energy delivery, the at least one energy delivery electrode is in close proximity with the target tissue.

14 Claims, 9 Drawing Sheets

Related U.S. Application Data

(60) Provisional application No. 62/091,760, filed on Dec. 15, 2014.

(51) Int. Cl.
  *A61B 18/00* (2006.01)
  *A61N 1/32* (2006.01)
  *A61B 90/00* (2016.01)

(52) U.S. Cl.
  CPC .............. *A61B 2018/00357* (2013.01); *A61B 2018/00577* (2013.01); *A61B 2018/00613* (2013.01); *A61B 2018/00648* (2013.01); *A61B 2018/00702* (2013.01); *A61B 2018/00708* (2013.01); *A61B 2018/00761* (2013.01); *A61B 2018/00791* (2013.01); *A61B 2018/00797* (2013.01); *A61B 2018/00827* (2013.01); *A61B 2018/00839* (2013.01); *A61B 2090/065* (2016.02); *A61N 1/327* (2013.01)

(58) Field of Classification Search
  CPC  A61B 2018/00357; A61B 2018/00577; A61B 2018/00613; A61B 2018/00648; A61B 2018/00702; A61B 2018/00708; A61B 2018/00761; A61B 2018/00791; A61B 2018/00797; A61B 2018/00827; A61B 2018/00839; A61N 1/327
  USPC ....................................................... 606/32, 34
  See application file for complete search history.

(56) References Cited

U.S. PATENT DOCUMENTS

| | | |
|---|---|---|
| 8,048,067 B2 | 11/2011 | Davalos et al. |
| 8,114,070 B2 | 2/2012 | Rubinsky et al. |
| 8,221,411 B2 | 7/2012 | Francischelli et al. |
| 8,282,631 B2 | 10/2012 | Davalos et al. |
| 8,500,713 B2 | 8/2013 | Ferek-Petric |
| 8,603,087 B2 | 12/2013 | Rubinsky et al. |
| 8,620,423 B2 | 12/2013 | Demarais et al. |
| 2002/0169445 A1 | 11/2002 | Jain et al. |
| 2003/0204161 A1 | 10/2003 | Ferek-Petric |
| 2005/0171523 A1 | 8/2005 | Rubinsky et al. |
| 2005/0171574 A1 | 8/2005 | Rubinsky et al. |
| 2005/0261672 A1 | 11/2005 | Deem et al. |
| 2006/0200118 A1 | 9/2006 | Krishnan et al. |
| 2007/0043345 A1 | 2/2007 | Davalos et al. |
| 2007/0156135 A1 | 7/2007 | Rubinsky et al. |
| 2008/0015571 A1 | 1/2008 | Rubinsky et al. |
| 2008/0132884 A1 | 6/2008 | Rubinsky et al. |
| 2008/0132885 A1 | 6/2008 | Rubinsky et al. |
| 2008/0269586 A1 | 10/2008 | Rubinsky et al. |
| 2008/0281312 A1* | 11/2008 | Werneth ............. A61B 18/1492 606/33 |
| 2008/0312673 A1 | 12/2008 | Viswanathan et al. |
| 2010/0174282 A1 | 7/2010 | Demarais et al. |
| 2010/0305462 A1* | 12/2010 | Callas ................. A61N 1/3702 600/521 |
| 2011/0166499 A1 | 7/2011 | Demarais et al. |
| 2011/0245756 A1 | 10/2011 | Arora et al. |
| 2012/0059255 A1 | 3/2012 | Paul et al. |
| 2012/0071784 A1 | 3/2012 | Davalos et al. |
| 2012/0277741 A1 | 11/2012 | Davalos et al. |
| 2013/0030430 A1* | 1/2013 | Stewart ................. A61N 1/327 606/41 |
| 2013/0110098 A1 | 5/2013 | Lalonde |
| 2013/0158509 A1 | 6/2013 | Consigny et al. |
| 2013/0196441 A1 | 8/2013 | Rubinsky et al. |
| 2013/0197425 A1 | 8/2013 | Golberg et al. |
| 2013/0345779 A1 | 12/2013 | Maor et al. |
| 2014/0066913 A1 | 3/2014 | Sherman |
| 2014/0107539 A1 | 4/2014 | Zarins et al. |

FOREIGN PATENT DOCUMENTS

| | | |
|---|---|---|
| WO | 2005065284 A2 | 7/2005 |
| WO | 2007079438 A2 | 7/2007 |
| WO | 2008070413 A2 | 6/2008 |
| WO | 2008070521 A2 | 6/2008 |
| WO | 2011153164 A1 | 12/2011 |
| WO | 2015171921 A2 | 11/2015 |

OTHER PUBLICATIONS

International Search Report and Written Opinion dated Mar. 4, 2016, for corresponding International Application No. PCT/US2015/061335; International Filing dated Nov. 18, 2015 consisting of 12-pages.

* cited by examiner

TIMED ENERGY DELIVERY

CROSS-REFERENCE TO RELATED APPLICATION

This application is a divisional of U.S. application Ser. No. 14/664,269, filed Mar. 20, 2015, entitled "TIMED ENERGY DELIVERY", now U.S. Pat. No. 10,271,893, issued on Apr. 30, 2019, which claims the benefit of U.S. Provisional Patent Application Ser. No. 62/091,760, filed Dec. 15, 2014, entitled "TIMED ABLATION ENERGY DELIVERY, the entirety of which is incorporated herein by reference.

FIELD

The present application relates to a method and system for mapping tissue and producing lesions for the treatment of cardiac arrhythmias in a non-thermal and optimal manner, minimizing the amount of energy required to selectively stun or ablate the target tissues. Energy may be delivered only at the moment(s) of best device position and proximity of an electrode to target tissue, and only during a time in the cardiac cycle determined to be optimal for reversible or irreversible effects. Complications associated with thermal ablation techniques may be eliminated.

BACKGROUND

Tissue ablation is a medical procedure commonly used to treat conditions such as cardiac arrhythmia, which includes atrial fibrillation. For treating cardiac arrhythmia, ablation can be performed to modify tissue, such as to stop aberrant electrical propagation and/or disrupt aberrant electrical conduction through cardiac tissue. Although thermal ablation techniques are frequency used, such as cryoablation and radiofrequency (RF) ablation, non-thermal techniques such as pulsed field ablation (PFA) may also be used.

Pulsed field ablation involves the application of short pulsed electric fields (PEF), which may reversibly or irreversibly destabilize cell membranes through electropermeablization but generally do not affect the structural integrity of the tissue components, including the acellular cardiac extracellular matrix. The nature of PFA allows for very brief periods of therapeutic energy delivery, on the order of tens of milliseconds in duration. Further, PFA may not cause collateral damage to non-target tissue as frequently or as severely as thermal ablation techniques. Additionally, pharmacologic agents may be preferentially introduced into the cells of targeted tissue that are exposed to PEF having reversible membrane permeablization.

However, all intracardiac stimulation, recording, and ablation catheters are affected by cardiac motion, respiratory motion, device stiffness/maneuverability, and random patient movements. These sources of motion affect the quality of electrode contact with, for example, the heart wall. During energy delivery to ablate the target tissue, this motion can reduce effectiveness of such deliveries during the periods when the electrodes move away from the target tissue.

It is therefore desirable to provide a system and method for evaluating the quality of electrode-tissue contact. More specifically for PFA, it is desirable to provide a system and method for delivering energy to target tissue only when the electrodes are in good proximity to the target tissue and the timing within the cardiac cycle is optimal. This differs from the requirement for good thermal contact with tissue when using RF energy to perform hyperthermal ablations. Effective ablation of tissue using PFA only requires that the electric field must encompass the targeted area of ablation in order to cause ablation. In a similar manner, reversible permeablization effects may be imposed in target tissues when PEF encompasses the targeted area of tissue.

SUMMARY

The present application advantageously provides a method and system for delivering pulsed field energy to a target tissue site selectively when there is good proximity between one or more energy delivery electrodes and the target tissue and when the patient's cardiac cycle is at an optimal time for ablation. A method of treating target tissue of a patient's heart, which may have a cardiac cycle, with pulsed field energy may include determining timing of the cardiac cycle and an optimal time within the cardiac cycle for energy delivery; evaluating proximity between at least one energy delivery electrodes and the target cardiac tissue; and delivering pulsed field energy from the at least one energy delivery electrodes to the target tissue when, during the optimal time for energy delivery, the at least one energy delivery electrode is in proximity to the target cardiac tissue. The cardiac cycle timing may be determined using body surface electrocardiograms or intracardiac electrograms. The heart may include a ventricle, and determining the optimal time within the cardiac cycle for energy delivery may include identifying depolarization of the ventricle and repolarization of the ventricle within the cardiac cycle. Further, energy may be delivered to the target tissue after depolarization of the ventricle and before repolarization of the ventricle. Determining cardiac cycle timing may further include measuring a QT interval that includes an R wave, an S wave, and a T wave, and determining the optimal time within the cardiac cycle for pulsed field energy delivery may include identifying an ST segment within the QT interval. Pulsed field energy may be delivered during the ST segment so the delivery does not induce an arrhythmia. Further, the energy delivery to the target tissue may be initiated approximately 60-120 milliseconds after an onset of the R wave and terminated before an onset of the T wave. The delivered pulsed field energy may cause reversible or irreversible effects in the target tissue. For example, reversible effects in the target tissue may be caused when the pulsed field energy delivered to the target tissue is at most approximately 200 V and is delivered in one to 20 pulses. Conversely, irreversible effects in the target tissue may be caused when the pulsed field energy delivered to the target tissue is at least approximately 300 V and is delivered in one to 20 pulses or more. Each of the at least one energy delivery electrode may include a temperature sensor, the evaluation of contact between the at least one energy delivery electrode and the target tissue being based on a temperature measurement recorded by the at least one temperature sensor immediately following the delivery of pulsed field energy. Additionally or alternatively, the evaluation of proximity between the at least one energy delivery electrode and the target tissue may be based on at least one of: intracardiac electrogram amplitude measured in the target tissue; unipolar electrograms measured in the target tissue; the presence of a monophasic action potential measured using unipolar electrograms measured in the target tissue, the presence of a monophasic action potential indicating direct contact between the at least one energy delivery electrode and the target tissue; the ability of bipolar or unipolar pacing pulses delivered by the at least one energy delivery electrode to achieve cardiac capture through local myocardial stimulation within the target tissue, achieving cardiac capture indicating contact between the at least one energy delivery electrode and the target tissue; the amplitude threshold of bipolar or unipolar pacing pulses delivered by the at least one energy delivery electrode to achieve cardiac capture through local myocardial stimulation within the target tissue; responses of nerve or muscle tissue proximate the target tissue to energy stimuli delivered by the at least one energy delivery electrode; electrode-tissue contact force measurements; temperature response to low-level energy sufficient to produce measurable heating in contacted target tissue; low-frequency impedance magnitude measurements; high-frequency impedance magnitude measurements; high-frequency impedance phase angle measurements; current measured during pulsed field energy delivery; an instantaneous stability of the at least one energy delivery electrode as measured from at least one accelerometer in an energy delivery device; and the location of each of the at least one energy delivery electrode in real time, based on at least one of: electric (field) potential measurements to determine a 3D location of the at least one energy delivery electrode within the heart; electromagnetic navigation measurement to determine a 3D position of the at least one energy delivery electrode within the heart; electromagnetic or electric field navigation in relation to anatomical sites identified by body surface mapping to be target sites for energy delivery to treat arrhythmias; electromagnetic or electric field navigation in relation to anatomical sites identified by non-contact intracardiac sensing or multi-electrode intracardiac endocardial mapping to be target sites for energy delivery to treat arrhythmias; ultrasonic transmitting and receiving elements of a first medical device and ultrasonic transmitting, receiving, or echogenic elements in a second medical device in relation to anatomical sites identified by non-contact intracardiac sensing or multi-electrode intracardiac endocardial mapping to be target sites for energy delivery to treat arrhythmias; and ultrasound elements incorporated into a treatment device in relation to anatomic sites identified by non-contact or intracardiac sensing or multi-electrode intracardiac endocardial mapping to be target sites for energy delivery to treat arrhythmias.

A method of delivering pulsed field energy to target tissue of a patient's heart, the heart having a cardiac cycle, may include identifying a QT interval of the cardiac cycle, the QT interval including at least a Q wave, an R wave, an S wave, a T wave, and an ST segment between the S wave and an onset of the T wave; determining an optimal time within the cardiac cycle for pulsed field energy delivery, the optimal time being during at least a portion of the ST segment; delivering pulsed field energy from an electrode array of an energy delivery device to the target tissue during the optimal time for pulsed field energy delivery to cause reversible effects in the target tissue; and delivering pulsed field energy from the electrode array to the target tissue during the optimal time for pulsed field energy delivery to cause irreversible effects in the target tissue. For example, the pulsed field energy may be delivered to from the electrode array to the target tissue to cause irreversible effects in the target tissue in a first delivery between approximately 60 milliseconds after an onset of the R wave and approximately 120 milliseconds after the onset of the R wave. The electrode array may have an at least substantially circular configuration and may include nine energy delivery electrodes. The pulsed field energy may be delivered in bipolar mode between odd-numbered energy delivery electrodes (that is, between a first and a third electrode, between the third and a fifth electrode, between the fifth and a seventh electrode, and between the seventh and a ninth electrode) and between even-numbered energy delivery electrodes (that is, between a second and a fourth electrode, between the fourth and a sixth electrode, and between the sixth and an eighth electrode). Alternatively, pulsed field energy may be delivered in bipolar mode between energy delivery electrodes in a first portion of the electrode array and energy delivery electrodes in a second portion of the electrode array. Additionally or alternatively, the pulsed field energy may be delivered in unipolar mode between any of the energy delivery electrodes and a ground patch. The method may further include evaluating proximity between at least one energy delivery electrode and the target tissue, the pulsed field energy being delivered from the electrode array to cause irreversible effects in the target tissue during the optimal time for pulsed field energy delivery and when the at least one energy delivery electrode is in close proximity to the target tissue.

A system for treating target tissue of a patient's heart with pulsed field energy, the heart having a cardiac cycle, may include: an energy delivery device including an at least substantially circular electrode array having a plurality of energy delivery electrodes; and a control unit including a pulsed field energy delivery generator, the control unit being programmed to: determine timing of the cardiac cycle; determine an optimal time within the cardiac cycle for pulsed field energy delivery; evaluate proximity between at least one energy delivery electrode and the target tissue; and deliver pulsed field energy from the electrode array to the target tissue when, during the optimal time for pulsed field energy delivery, at least one of the plurality of energy delivery electrodes is in close proximity with the target tissue. Delivering pulsed field energy from the electrode array to the target tissue may include delivering pulsed field energy that causes reversible effects in the target tissue, such as when deliver pulsed field energy from the electrode array to the target tissue when, during the optimal time for pulsed field energy delivery, at least one of the plurality of energy delivery electrodes is in close proximity with the target tissue, or may be delivered such that it causes irreversible effects in the target tissue, such as when the pulsed field energy delivered to the target tissue is approximately 200 V or less and is delivered in one to 20 pulses, or the pulsed field energy may cause irreversible effects in the target tissue, such as when the pulsed field energy delivered to the target tissue is approximately 300 V or more and is delivered in at least one to 20 pulses. Determining the timing of the cardiac cycle may include evaluating a surface electrocardiogram having a Q wave, an R wave, an S wave, and a T wave, the control unit being programmed to deliver the pulsed field energy to the target tissue between approximately 60 milliseconds and approximately 120 milliseconds after an onset of the R wave. Additionally or alternatively, determining the timing of the cardiac cycle may include evaluating a surface electrogram having a Q wave, an R wave, an S wave, and a T wave, the control unit being programmed to deliver the pulsed field energy to the target tissue between the S wave and an onset of the T wave.

BRIEF DESCRIPTION OF THE DRAWINGS

A more complete understanding of the present application, and the attendant advantages and features thereof, will be more readily understood by reference to the following detailed description when considered in conjunction with the accompanying drawings wherein.

DETAILED DESCRIPTION

Figure 1:
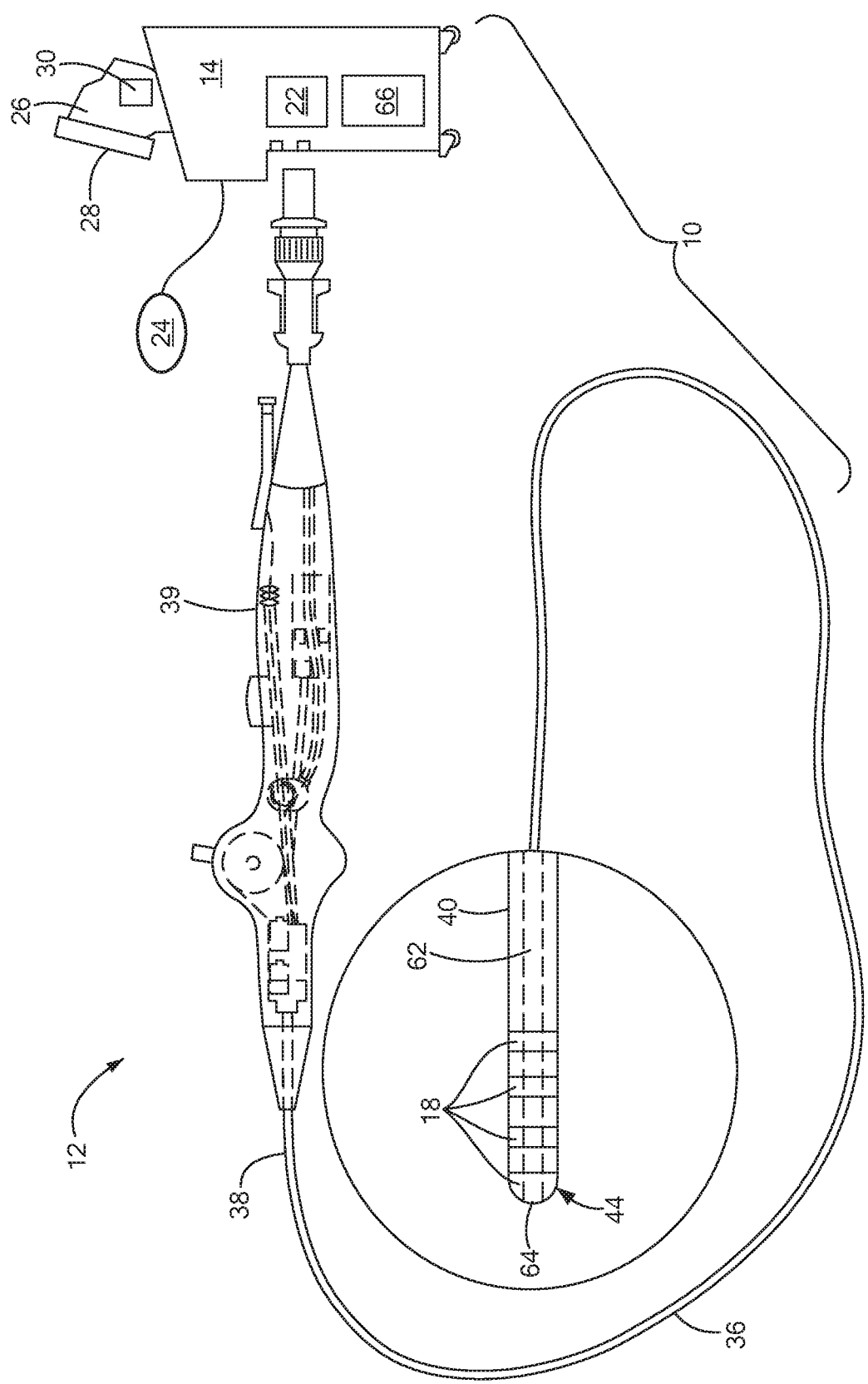
FIG. 1 shows an exemplary medical system for the application of energy to target tissue, the system having an energy delivery device.
Figure 3:
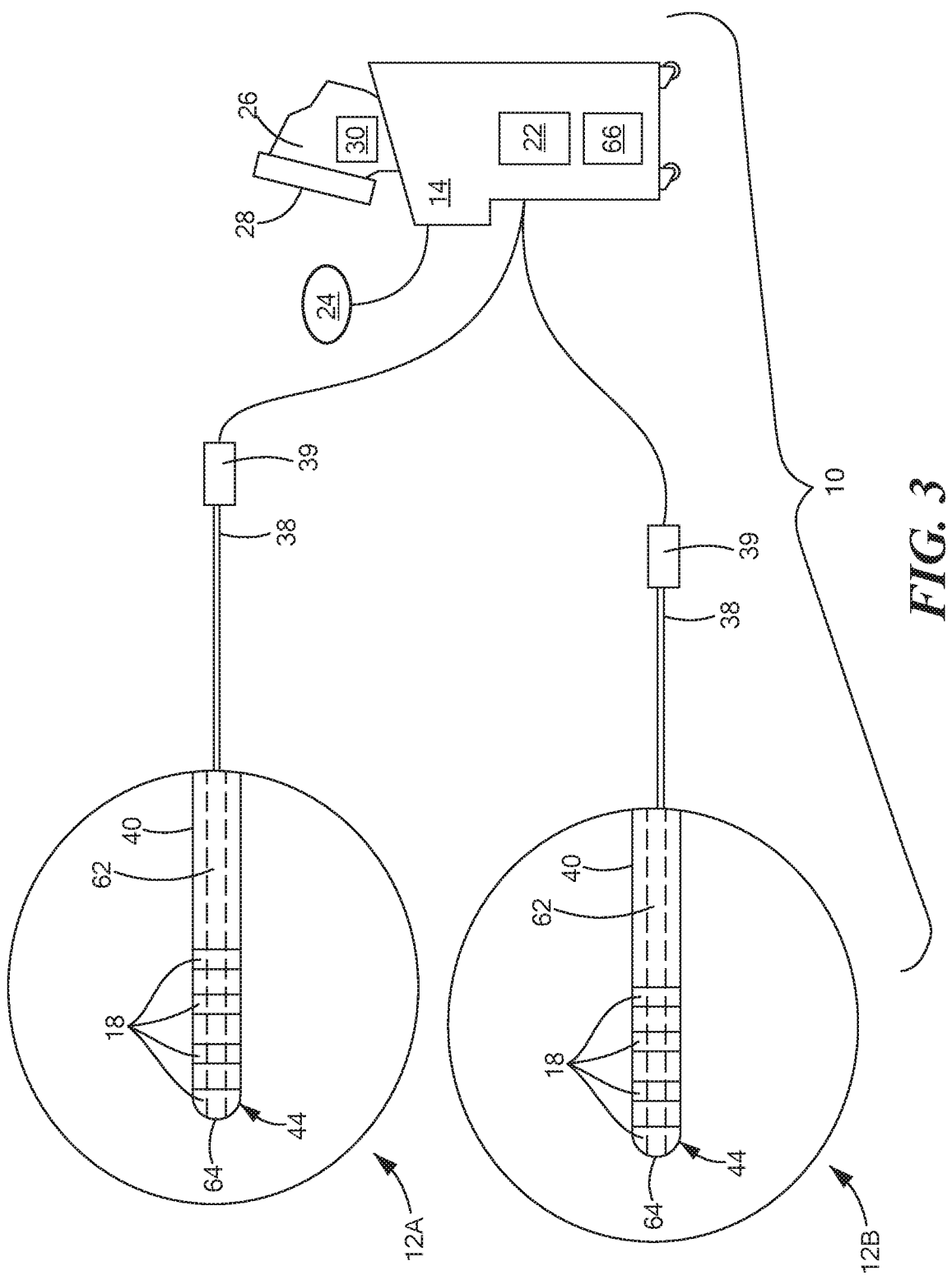
FIG. 3 shows an exemplary medical system for the application of energy to target tissue, the system having a first energy delivery device and a second energy delivery device.

Referring now to FIG. 1, an exemplary medical system for delivering energy to target tissue is shown. The system 10 may be used to treat endocardial surfaces, but it will be understood that the system may be used to treat other areas, including epicardial tissue, esophageal tissue, dermal tissue, bronchial tissue, lung tissue, soft tissues, tumors, and any other tissue that is treated with the application of energy and is affected by cardiac motion, respiratory motion, random patient movements, and/or other factors that may affect electrode-tissue contact. The system 10 may generally include an energy delivery device 12 and a control unit 14. However, more than one delivery device may be used (for example, as shown in FIGS. 3-4B). The energy delivery device 12 may include one or more energy delivery electrodes 18 for delivering an electrical current, and may further include one or more electrodes such as mapping electrodes, PFA electrodes, and/or electrodes for measuring characteristics such as impedance (not shown).

The device 12 and/or system 10 may also include one or more sensors 20, such as temperature sensors, pressure sensors, piezoelectric elements, strain gauges, and/or fiber bragg sensors. For example, motion, force, or acceleration detectors may be of various designs such as piezoelectric, capacitive, inertial, or optical. In some embodiments, the system 10 may include one or more secondary devices, such as an indwelling catheter or pacemaker, secondary treatment catheter, or other devices. For example, the secondary device may be an indwelling catheter. Further, as shown and described in more detail in FIG. 3, the system 10 may include a first energy delivery device 12A and a second energy delivery device 12B.

The term "control unit" may be used to generally refer to any system components that are not part of the delivery device. The control unit 14 may be described to include system components that are physically located within or integrated with an operator unit or are in communication with an operator unit. The control unit 14 may be configured to deliver pulsed field electrical energy for the treatment of tissue using pulsed field ablation (PFA). PFA is a non-thermal treatment method, so challenges associated with effective conventional thermal ablations (such as radiofrequency or cryoablation) may be eliminated. Specifically, tissue heating or cooling is not required, and the risk of producing coagulum or char may be eliminated. Additionally, the procedure time may be dramatically shortened because total duration of PFA energy delivery may require less than a minute for a typical procedure, versus 20-40 minutes for thermal ablation. PFA with timed ablation energy delivery may reduce the technical complexity of energy delivery device positioning, since tissue contact or proximity to target tissue may be sensed by the device 12 and energy gated to only be delivered at moments of optimal contact or target tissue proximity. PFA may eliminate the risk of thermal complications (such as char or coagulation) and undesirable trauma to cardiac and nearby structures (such as the esophagus, pulmonary vein walls, coronary arteries, or phrenic nerve) because the energy pulse selectively and specifically targets primarily cardiac muscle cells. Optionally, the control unit 14 may also be configured to deliver RF energy, microwave energy, laser energy, ultrasound energy, and/or may be configured for use in cryotreatment procedures. In addition to the timed energy delivery for ablation of cardiac tissue, timed energy delivery may be used to treat other tissues exhibiting movement, such as the airways, using the methods described herein, but in relation to respiratory motion.

Further, control unit 14 may include an energy generator 22 in electrical communication with one or more delivery electrodes 18, and the energy generator 22 may also be in electrical communication with one or more mapping or other electrodes (not shown). The energy generator 22 may be able to deliver high frequency non-ablative pulses for stimulating the autonomic nervous system or inherent automaticity in the substrate to which the energy is delivered. The generator 22 may also be able to deliver stimulation pulses in the range of approximately 0.1 millisecond to 10 milliseconds in duration and at frequencies of approximately 20 Hz to 2000 Hz. Further, the generator 22 and/or control unit 14 may be configured such that the operator is able to modulate the amplitude of the biphasic square-wave stimulation pulses from between 0 V and 200 V peak voltage, and such that the operator is able to deliver pulsed stimulation continuously or intermittently from the generator while reserving the ability to switch to ablation energy at any desired moment. This may give the operator the ability to either perform mapping of part or all of a heart chamber before delivering ablation energy or to perform ablation at each or selected sites of, for example, ectopy or atrioventricular (A-V) nodal response as such sites are found and before moving to new sites. Still further, the energy generator 22 and/or control unit 14 may have an automated system, selectable by the operator, whereby ectopy, when detected may activate the ablation system to deliver ablative energy upon each detection of, for example, ectopic activity while moving the device on tissue sites and delivering pulsed stimulation to elicit ectopic responses. Similarly, the generator 22 and/or control unit 14 may be able to automatically determine optimal timing of ablative energy deliveries.

The response to stimulation may be manifested in a slowing of A-V nodal conduction or in the form of premature atrial contractions (ectopic activity). Such responses may be monitored by an electrophysiology (EP) recording system, which may be a component of the control unit 14. Additionally, such responses may be quantified by the recording system and the data transferred from the recording system to the generator 22 and/or the control unit 14, for example, an interface with a cardiac navigation system (that may also be a component of the control unit 14) that places the data into an anatomical display. Data that describes the nature of the heart muscle in the specific location where the response was elicited may be useful to the operator for determining target tissue for ablation. Areas of high ectopic activity or A-V nodal response may be desired targets for ablation in order to effectively treat atrial fibrillation and other arrhythmias.

The control unit 14 may also include a skin surface ground electrode patch 24 (also referred to as a ground electrode or patient return electrode) that may be in contact with the patient's skin during an energy delivery procedure, such as when energy is delivered in unipolar mode. Further, the control unit 14 may include a user interface by which the operator may select the energy delivery mode, monitor energy delivery parameters, adjust or stop energy delivery, and/or select one or more electrodes to which to deliver energy. For example, the user interface may include a foot pedal, mouse, joystick, one or more computers 26 one or more displays 28, buttons, knobs, touchpads, touchscreens, or other input means, optionally located on the energy delivery device 12 handle. Although the system 10 and energy delivery may be completely automated, the operator may control the form of the energy waves, on/off status of individual electrodes 18, and/or delivery voltage through the user interface. Proposed timing of energy deliveries may be indicated to the operator by, for example, imposing markers on the cardiac electrogram recording system to indicate when delivery of a pulse train will commence during the cardiac cycle once executed by the operator. Such information may be communicated to the operator using the one or more displays 28.

The control unit 14 may further include one or more processors 30 programmed to receive, process, and/or communicate data received from the one or more energy delivery devices 12, one or more secondary devices, and/or other components of the system 10. The control unit 14 may further be programmed to receive and process data (for example, electric potential measurements and/or electromagnetic navigation measurements), and determine a 3D position of the device 12 within the heart.

Figure 2:
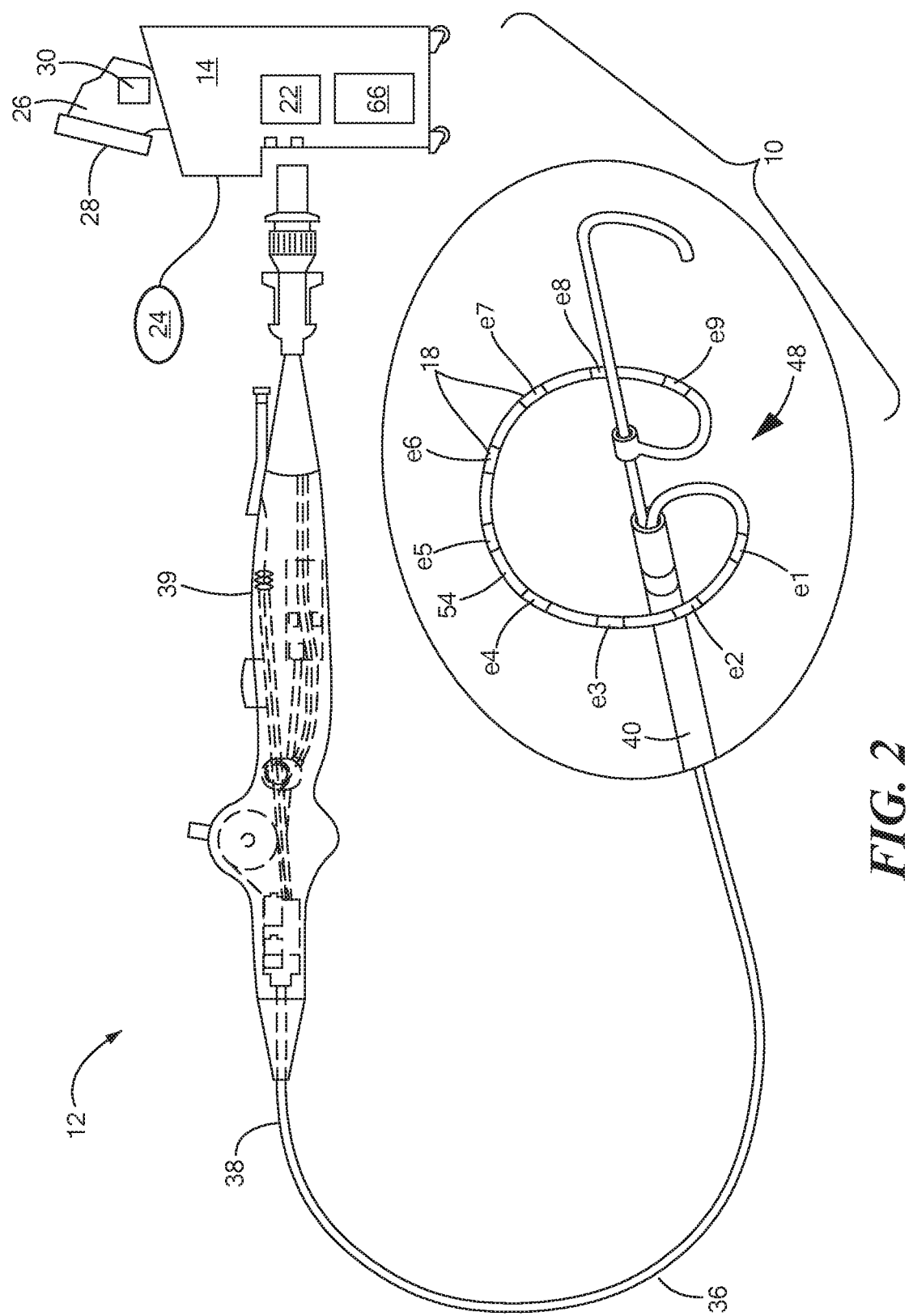
FIG. 2 shows an energy deliver device having a substantially circular multi-electrode array for delivering energy to target tissue, such as about a vessel ostium.

Referring now to FIGS. 1 and 2, the energy delivery device 12 may include an elongate body 36 having a proximal portion 38, which may be coupled to a handle 39, and a distal portion 40. The one or more delivery electrodes 18 may be coupled to, located on, integrated with, or otherwise within the distal portion 40 of the delivery device 12. Further, the distal portion 40 of the delivery device 12 may have any of a variety of configurations. For example, FIG. 1 shows a focal device having a plurality of electrodes 18, including an electrode 18 located at the distal tip 44 of the elongate body 36 and a plurality of electrodes 18 located along at least a portion of the elongate body distal portion 40, proximal to the distal tip 44. However, it will be understood that fewer or more electrodes than those shown in the figures may be used.

The device 12 shown in FIG. 2 may include a distal portion 40 that includes an electrode array 48 to or in which one or more electrodes 18 are coupled, affixed, attached, or otherwise incorporated. Further, one or more sensors, such as those discussed above, may be coupled to or located in the structure of the electrode array 48 or on or within the elongate body 36, and may also be included on or within the elongate body 36 of a focal-type device as shown in FIG. 1. The distal portion 40 may include a shaft 50 slidably and rotatably movable within the elongate body 36. The electrode array 48 may also include a flexible carrier arm 54, a distal portion of which being coupled to the shaft 50 and a proximal portion of which being coupled to the elongate body distal portion 40, such that longitudinal movement and/or rotation of the shaft 50 within the elongate body 36 may adjust the configuration of the electrode array 48. For example, advancement of the shaft 50 distally may cause the electrode array 48 to have a linear or at least substantially linear configuration (not shown) that may be used for delivery of the device to the target site, whereas retraction of the shaft 50 may cause the carrier arm 54 to expand radially from the shaft 50 and assume an at least substantially circular configuration (as shown in FIG. 2). Further, the diameter of the at least substantially circular configuration of the carrier arm 54 may be adjusted by rotation of the shaft 50 within the elongate body 36. The carrier arm 54 may bear a plurality of delivery electrodes 18 along its length. This configuration may be used to deliver energy to, for example, a pulmonary vein ostium. It will be understood that fewer or more electrodes than those shown in the figures may be used, and alternative distal portion and/or electrode array configurations may be used. For example, an electrode array may include more than one carrier arm and/or may include one or more sensors, mapping electrodes, radiopaque markers, or other components.

The energy delivery device 12 may optionally include a fluid delivery lumen 62 extending from the elongate body proximal portion 38 to the elongate body distal portion 40, and may include one or more openings 64 in the distal portion 40, such as at or proximate the distal tip 44, as shown in FIG. 1. In this case, the control unit 14 may include a fluid reservoir 66 in fluid communication with the fluid delivery lumen 62. The fluid delivery lumen 62 may be used to deliver, for example, blood-vessel dilating drugs such as nitroglycerin, to resolve possible vessel spasm or constrictions that may occur upon energy. Additionally or alternatively, therapeutic pharmacologic agents may be administered through the fluid delivery lumen 62 to allow enhanced uptake of the therapeutic pharmacologic agents though electropermeablization.

Referring now to FIGS. 3-4B, the system 10 may include a first energy delivery device and a second energy delivery device. The first energy delivery device 12A and the second energy delivery device 12B shown in FIG. 3 may be similar to the device 12 shown in FIG. 1, although it will be understood that the system 10 may alternatively include a first and second energy delivery device that are similar to the device 12 shown in FIG. 2, or the system 10 may include two devices that are the same as each other but have configurations different than those shown in FIGS. 1 and 2, or that have configurations different from each other and that are the same as or different than those shown in FIGS. 1 and 2.

Figure 4A:
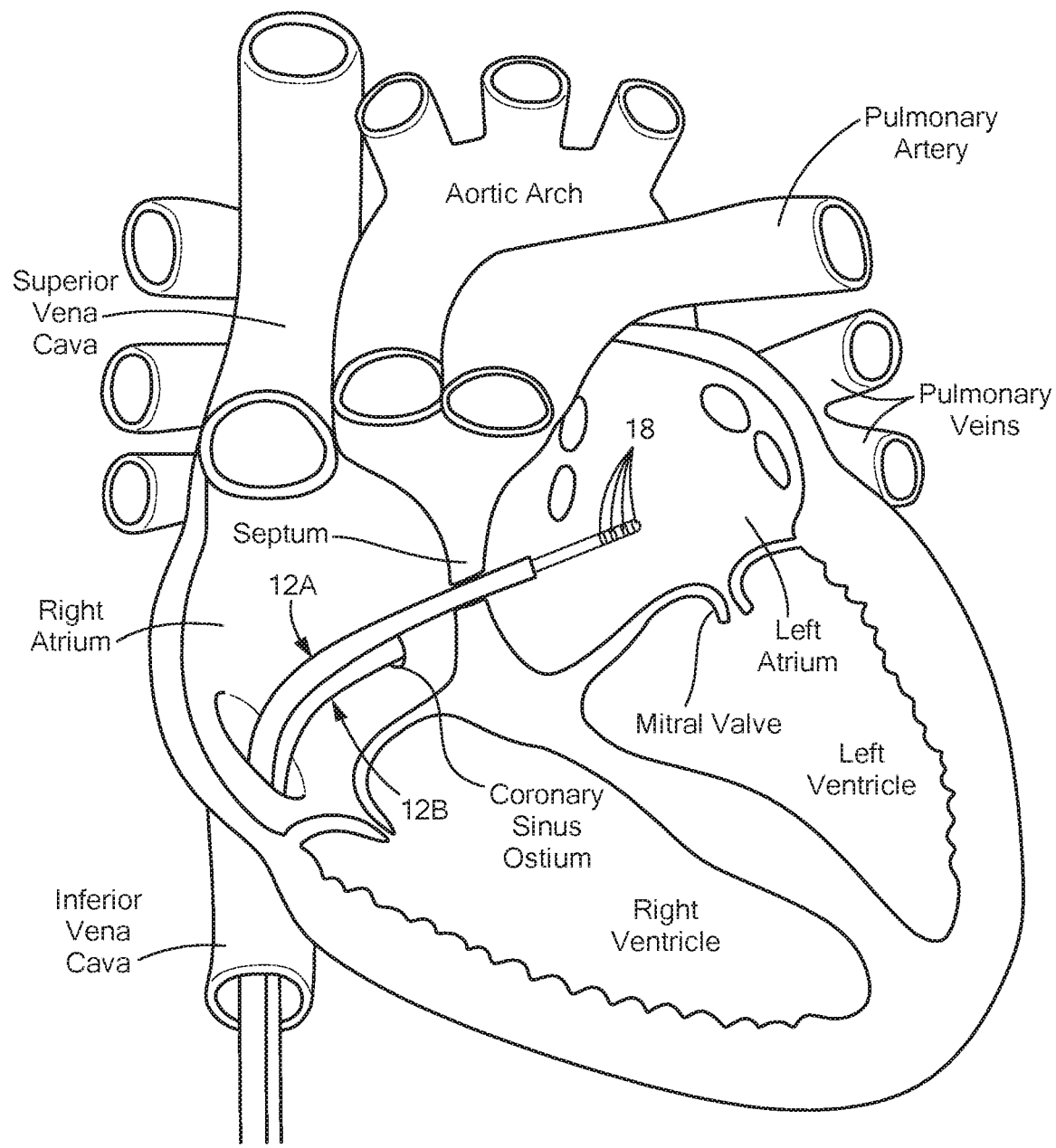
FIGS. 4A and 4B show a first energy delivery device and a second energy delivery device being used in combination to treat tissue.
Figure 4B:
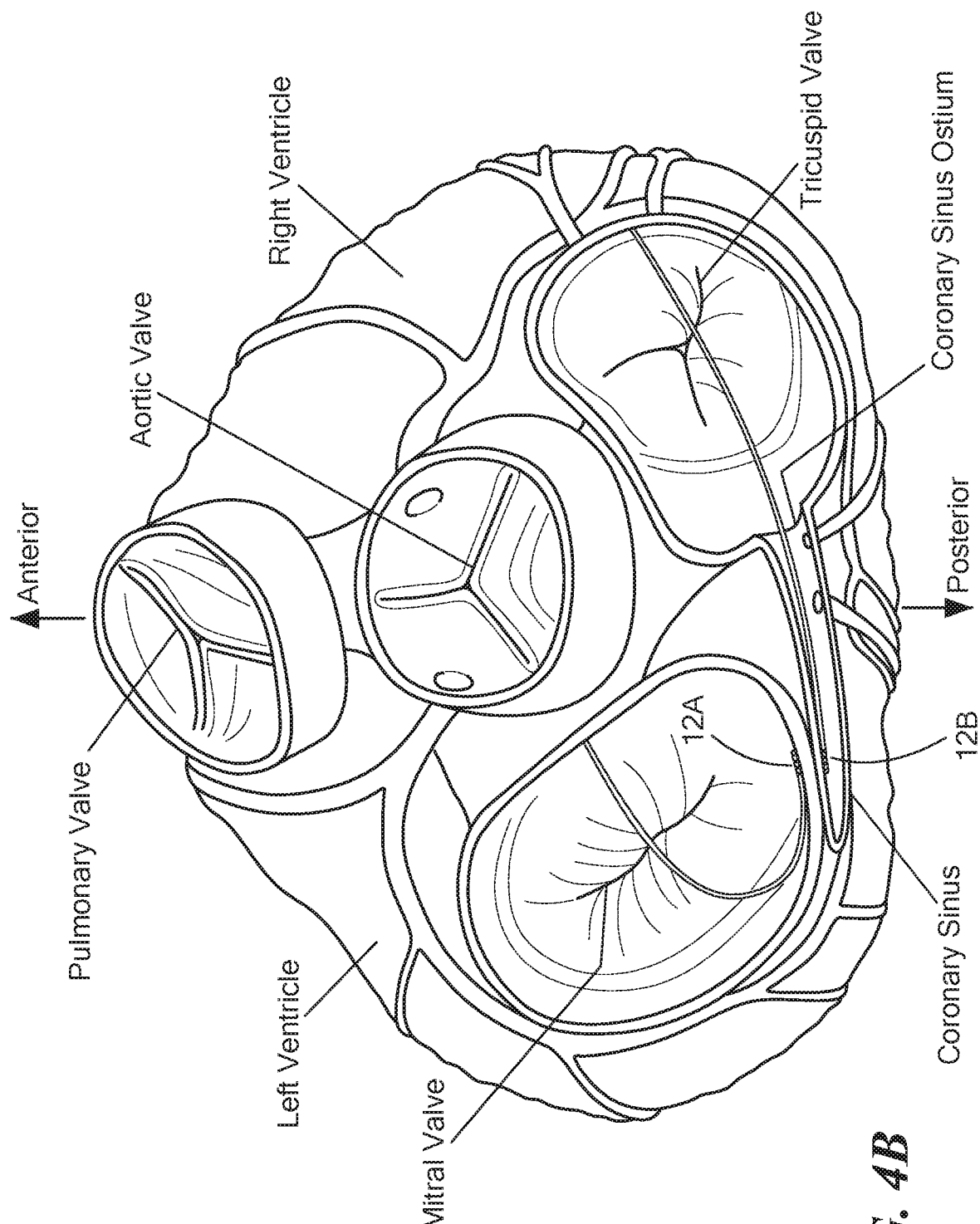

As shown in FIGS. 4A and 4B, two delivery devices 12A, 12B may be used to deliver energy to target tissue. Energy flow from electrodes 18 on a single delivery device may be configured to flow between every other electrode (for example, between even-numbered electrodes e2, e4 or between odd-numbered electrodes e1, e3 as shown in FIG. 1; or between even-numbered electrodes e2, e4, e6, e8 or between odd-numbered electrodes e1, e3, e5, e7 as shown in FIG. 2) if multiple electrodes 18 are present, or it may be configured to flow between one or more electrodes 18 and the skin surface ground electrode patch 24 on the patient. In some cases it may be desired to produce both bipolar energy flow between, for example, every other electrode 18 and some portion of unipolar energy flow between the electrodes 18 and the skin surface ground electrode patch 24. If electrodes 18 are too close together, energy may arc from one electrode to the other, but if electrodes 18 are too far apart, the ablation pattern may have gaps and the operator may have to reposition the device to create a contiguous lesion or may have to use higher voltages. So, energy may be delivered between odd-numbered electrodes in a first delivery and may be delivered between even-numbered electrodes in a second delivery, or vice versa. This may result in a contiguous lesion without the need to move the catheter and may provide optimal electrode spacing for sensing and pulsed field energy delivery.

In cases where more than one delivery device 12A, 12B is used (for example, as shown in FIGS. 3-4B), the energy may be directed to flow between the electrodes 18 of the first device 12A and the electrodes 18 of the second device 12A to reversibly or irreversibly affect tissue therebetween. If the electrode areas are of similar size, this is considered to be bipolar energy delivery. As a non-limiting example, the first delivery device 12A may be located inside a heart chamber and the second delivery device 12B may be located in another area of the heart but proximate the location of the first delivery device 12A, such as the pericardial space or coronary sinus or coronary vein. For example, FIGS. 4A and 4B show the second delivery device 12B as being located in the coronary sinus proximate the location of the first delivery device 12A that is located within the left atrium. Additionally or alternatively, energy may be delivered between the first delivery device 12A located within a coronary vein and the second delivery device 12B located within a coronary artery to first stun then, if desired, to ablate an area of cardiac tissue between the two devices 12A, 12B. As shown and described in FIG. 1, at least one of the first and second delivery devices 12A, 12B may optionally include a fluid delivery lumen 62 for the delivery of one or more treatment compounds.

Figure 5:
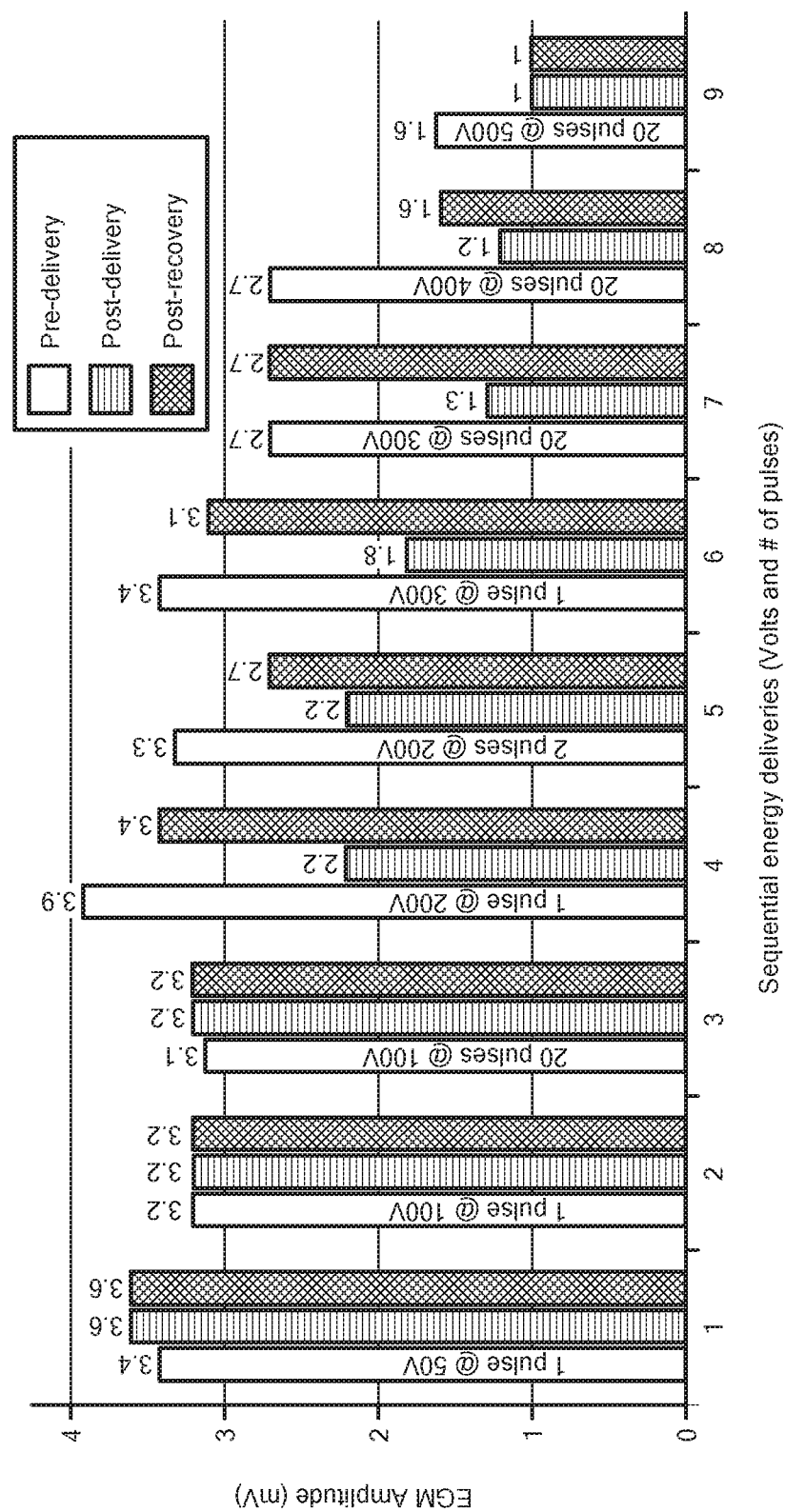
FIG. 5 shows data from sequential deliveries of pulsed filed energy, the deliveries first causing reversible effects and then reversible effects on cardiac tissue when sufficiently high electric field strengths were delivered to the cardiac tissue.

Energy deliveries may be selected to be reversible or irreversible in their effects on the targeted tissues. For example, FIG. 5 shows the results of porcine intracardiac experiments where pulsed field energy was delivered to a fixed site in the heart and measurements of heart muscle activity under the energy delivery electrodes was measured over the course of multiple energy deliveries. In the experiment from which the data in FIG. 5 was collected, a first level of energy was delivered by a delivery device 12 that caused reversible effects. Next, the level of energy delivered by the delivery device 12 was increased to cause irreversible effects on the cardiac tissue. In that experiment, a multi-electrode delivery device 12, such as that shown in FIG. 2, was positioned in the left atrial appendage (LAA). Before the delivery of energy to the target tissue, an electrogram (EGM) amplitude in millivolts was measured from one of the electrode pairs. Then bipolar energy was delivered from the device 12, using either one pulse or a train of 20 pulses. The EGM amplitude from the electrode pair was then re-measured after the energy had been delivered (referred to as a post-delivery measurement), and the EGM was again re-measured after approximately two minutes after the energy had been delivered (referred to as a post-recovery measurement). If the EGM was not reduced, a higher amplitude or a greater number of pulses was used in a subsequent energy delivery. A series of nine energy deliveries are shown in FIG. 5, with each delivery having an increased voltage and/or a greater number of pulses over the previous energy delivery. The pulsed field energy was delivered using a delivery device having a substantially circular electrode array 48 (such as the device shown in FIG. 2) having nine cylindrical, 3.0 mm-long delivery electrodes 18 spaced approximately 3.75 mm apart on the array 48, with the pulsed field energy delivery being made in a bipolar manner where every other electrode 18 is of the opposite polarity (odd- versus even-numbered electrodes forming the bipolar configuration). In addition, pulses were delivered in a biphasic manner, by alternating the polarity between every other electrode for every succeeding pulse, resulting in an alternating pulsed current. Time delay between positive and negative pulses may be zero or extended to hundreds of microseconds in a practical application. The results show that pulses delivered at up to 200 V had reversible effects on EGM amplitude, whereas voltages of 300 V or more and between 1 and 20 pulses were the minimum settings required to cause irreversible effects on EGM. This applied voltage of 300 V may produce a peak electric field strength of roughly 400 V/cm, depending on the types of surrounding tissues. Such potential for low energy stunning of underlying tissues may allow the operator to test the effect of energy delivery on an arrhythmia before delivering higher energy that will result in permanent or irreversible damage. Deliveries of high amplitude in multiple pulses may be used for irreversible ablation while lower amplitudes may merely stun the tissue. Once a suspected focal site of origin of an arrhythmia is identified, it may be advantageous to test the effect of stunning this suspected site before permanently destroying it. If the desired resolution of the arrhythmia results from stunning, a higher amplitude pulse train may be delivered to irreversibly ablate this site. This may be desirable when attempting to locate and ablate focal sources of arrhythmias of sites responsible for the support of rotating conduction wavefronts, such as in conduction rotors in atrial fibrillation.

Figure 6:
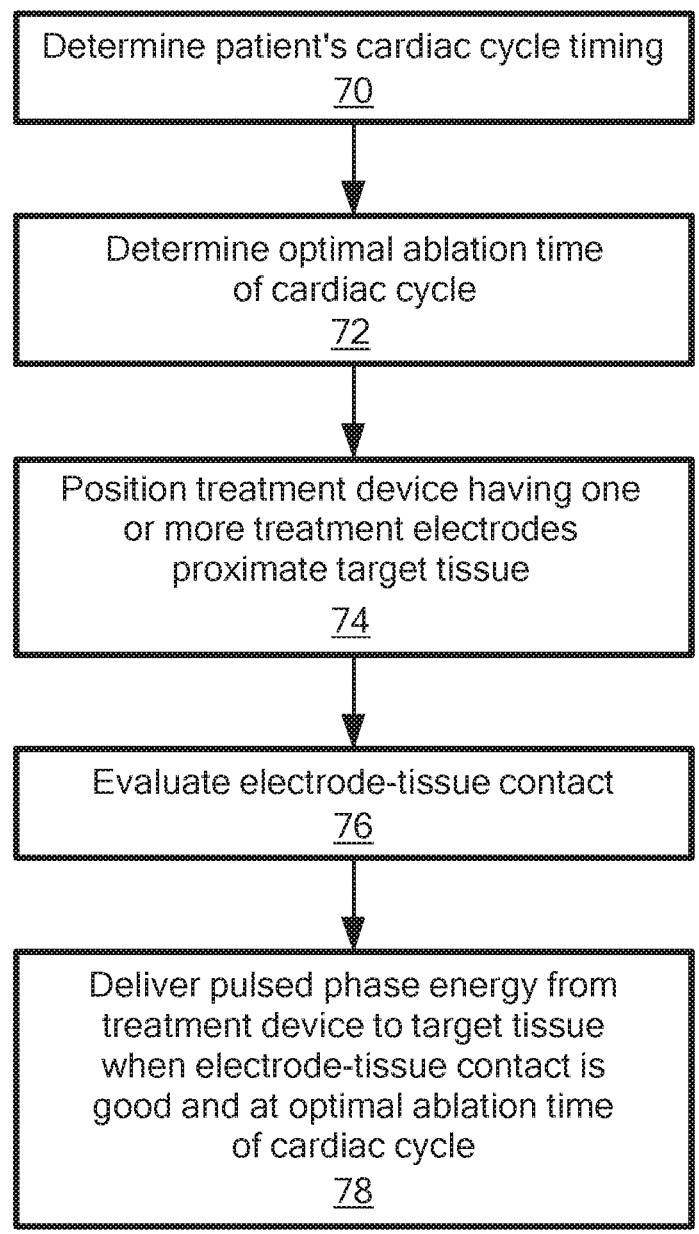
FIGS. 6 and 7 show flow charts of methods for delivering energy to target tissue.
Figure 7:
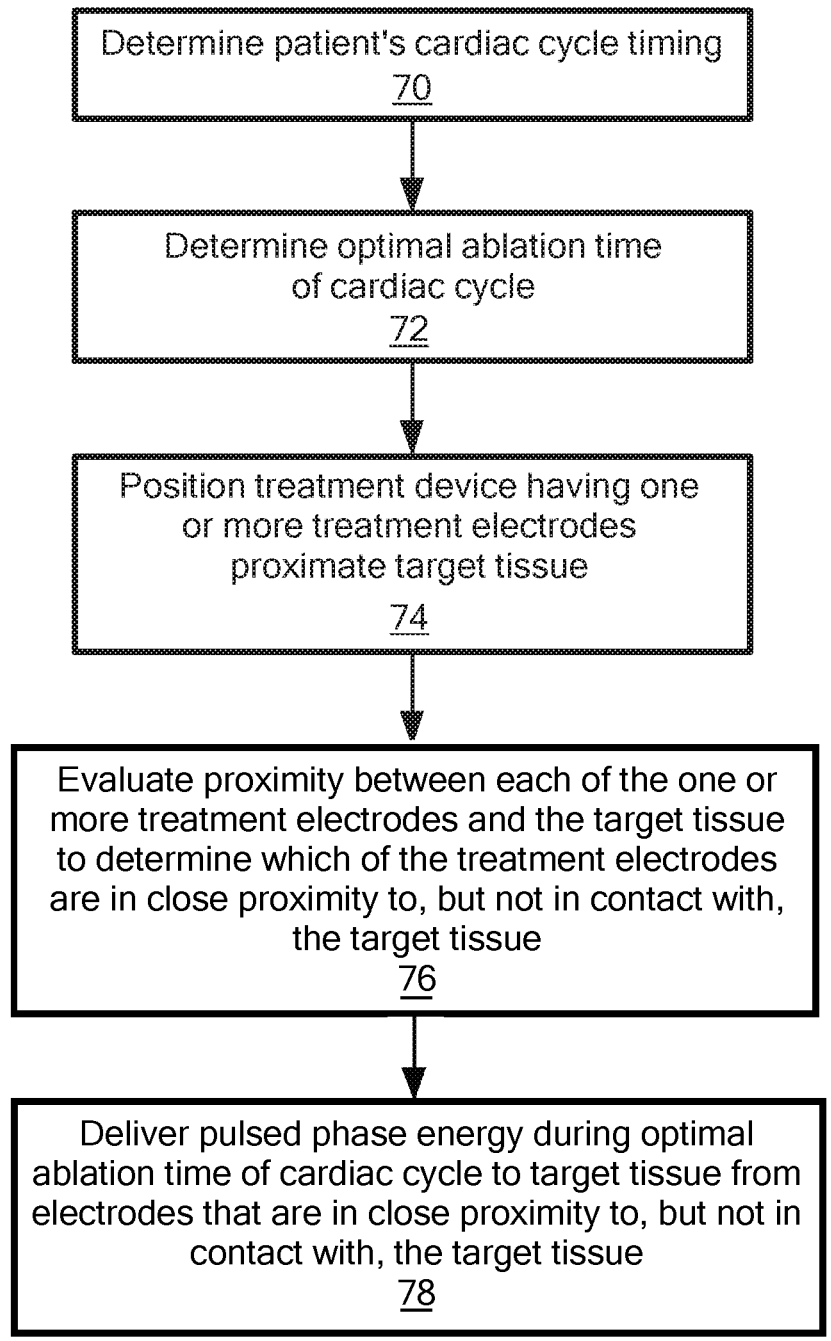

Referring now to FIGS. 6 and 7, flow charts for delivering energy to target tissue are shown. In general, various means of detecting quality of electrode-tissue contact (including proximity of electrodes to the target tissue) and/or motion of the ablation electrodes toward or away from the target tissue. Energy may then be delivered during times of optimal tissue contact, and delivery may be based on electrode-tissue contact in addition to timing within the cardiac cycle. For example, when the electrodes are in acceptable contact with the target tissue or in close proximity to the target tissue and the cardiac cycle is optimal, the energy will be delivered (for example, the delivery window shown in FIG. 8). FIG. 6 shows a flow chart of a first exemplary method in which energy is delivered from electrodes 18 when electrode-tissue contact is good and the cardiac cycle is optimal. FIG. 7 shows a flow chart of a second exemplary method in which energy is delivered from electrodes determined to be in close proximity to, but not in contact with, the target tissue and the cardiac cycle is optimal. By delivering only during this optimal period, ablation efficacy may be substantially improved. The present method may include two or more measured parameters for evaluating proximity to target tissue that, when analyzed together, may provide the optimal timing point for delivery of a therapeutic PFA pulse train. This may include recording impedance measurements indicating tissue contact status and/or navigation methods that track catheter motion. As a non-limiting example, the system 10 may continuously track the three-dimensional position in space of each of the energy delivery electrodes 18 of an electrode array 48 (for example, an at least substantially circular array 48 shown in FIG. 2) while one or more impedance measurements are recorded.

In the first step 70 of the method, the patient's cardiac cycle timing may be determined. For example, the cardiac cycle timing may be determined based on surface (for example, epicardium) electrocardiogram (ECG) measurements and/or based on intracardiac electrograms (EGMs). For example, the QT interval (a measure of the time between the start of the Q wave and the end of the T wave in the heart's electrical cycle, included in a QRST complex) may be measured and the timing of therapeutic energy delivery may be determined to ensure that it occurs after depolarization of the ventricles (which may be represented by the end of the S wave) has taken place but before repolarization (which may be represented by the beginning or onset of the T wave) of the ventricles has started. In a typical patient, the depolarization of the ventricles may take 100 milliseconds.

In the second step 72 of the method, the optimal ablation time within the cardiac cycle may be determined. The optimal time of delivery of reversible or irreversible therapeutic energy may be determined, for example, based on mapping of cardiac arrhythmias from one or more energy delivery devices 12, secondary indwelling catheters, and/or by a matrix of body surface electrodes. From such data streams, the optimal therapeutic energy delivery timing may be determined to interrupt the aberrant cardiac conduction circuit. Such deliveries may be timed to interrupt the cardiac condition, which may be rotating about a core region or meandering in the area of cardiac tissue. In addition, the origins of focal sites of activation may be detected by intracardiac multi-electrode arrays or body surface electrode-based maps of cardiac conduction. Sites of origin of such arrhythmias may then be targeted based on the location of the at least one energy delivery electrode 18 at the optimal timing of the cycle of cardiac motion or electrical activity.

Further, to enhance the effectiveness of pulsed field ablation energy in certain cases, it may be desired to create more extensively ablated regions. In such cases, the optimal timing of pulsed field delivery may be at multiple time points in the cardiac cycle. By delivering pulsed fields at more than one or multiple time points in the cardiac motion cycle, the effect of PFA may be more broadly distributed over a tissue surface. This may, in turn, result in a larger area of ablated myocardium. Such timing of multiple deliveries may be timed to coincide with a range of physical points in space attained during cardiac, respiratory, or other patient body motion. For example, the deliveries may be timed to coincide with the extremes of cardiac motion in each of the x, y, and z planes. Such deliveries may also be blanked or prevented from occurring during vulnerable periods of repolarization of the atrial or ventricular myocardium. Such energy deliveries may be selected to be reversible or irreversible in their effects on the targeted tissues. Deliveries of high amplitude in multiple pulses are used for irreversible ablation while lower amplitudes will result in reversible stunning of the tissue. Upon identifying a suspected focal site of origin of an arrhythmia, it may be of advantage to test the effect of stunning this suspected site before permanently destroying it. If the desired resolution of arrhythmia results from stunning, a higher amplitude pulse train may be delivered to irreversibly ablate this site. This technique may be desirable when attempting to locate and ablate focal sources of arrhythmias of sites responsible for the support of rotating condition wavefronts, such as in conduction of rotors in atrial fibrillation.

Figure 8:
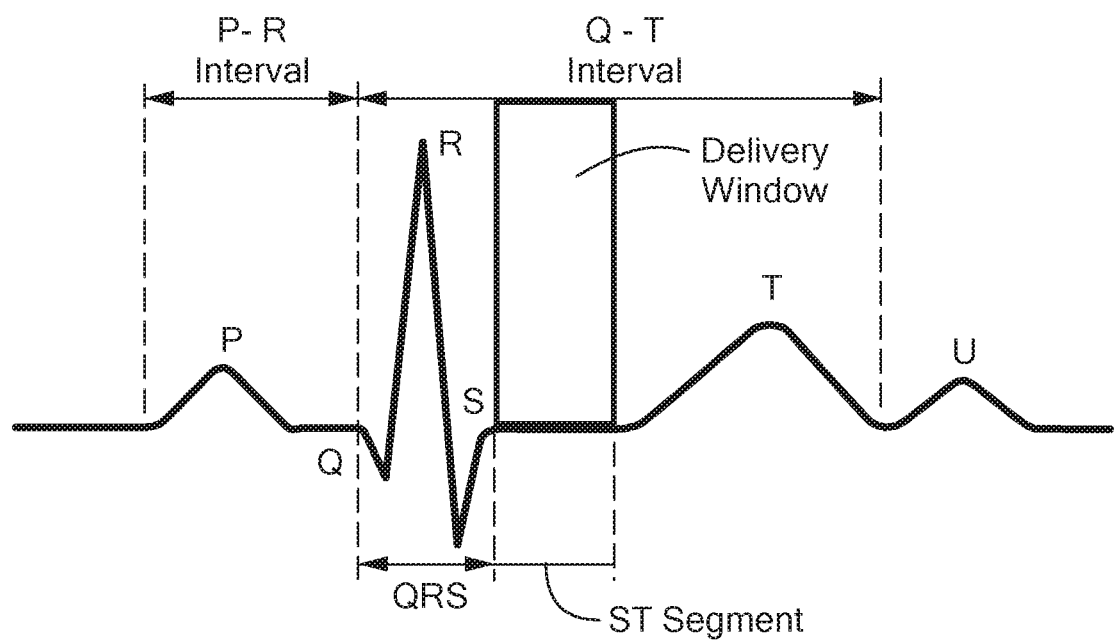
FIG. 8 shows an exemplary electrocardiogram of a cardiac cycle.

For example, timing of the delivery of therapeutic energy with the intent of ablating cardiac muscle while avoiding stimulation of the muscle, which could cause arrhythmias, may be timed to occur after the QRS complex is complete or nearly complete. As shown in FIG. 8, the surface electrocardiogram (ECG) may include a P wave, a Q wave, an R wave, an S wave, a T wave, and an ST segment between the S wave and the onset of the T wave. The R wave may represent an electrical stimulus as it passes through the main portion of the ventricular wall. An exemplary energy delivery timing may be at approximately 60-120 milliseconds after detection of the R wave so that the energy is delivered during at least a portion the ST segment. Energy delivery may be terminated before the onset of the T wave, regardless of what point during the ST segment at which energy delivery is initiated. This ST segment is referred to as the "delivery window" in FIG. 8. Energy may be delivered once during this time or it may be delivered multiple times, such as delivering energy a first time at approximately 80 milliseconds after detection of the R wave and delivering energy a second time at approximately 120 milliseconds after detection of the R wave. In this manner, energy may be delivered multiple times based, optionally, only during the ST segment and contact would not have to be evaluated after the initial contact assessment because energy delivery during this time may not induce arrhythmia. However, energy may be delivered sooner or longer after detection of the R wave. For example, the pulsed field energy may be spread to encompass a wider span of time by increasing the time delay between each pulse, such that the entire train of pulses fills the desired portion of time during the cardiac cycle in which it is deemed safe for delivery (such as the ST segment) or a much longer duration of more widely spaced pulses that encompass an entire cardiac cycle, such as when the energy delivery electrodes 18 are located in a site where it is unlikely to induce a ventricular arrhythmia. In such situations, the operator may select pulsed energy delivery to be spread over a wider span of time to effectively distribute the energy over a wider tissue surface. Correcting timing of the delivery and/or ensuring that the electrodes are remote from the ventricles may generally ensure that energy delivery does not induce an arrhythmia. For example, in the case of atrial fibrillation, energy delivery may be timed to occur immediately after the P wave of the atrium. However, in cases where it is deemed critical to ablate specific cells within the heart that are determined to be more susceptible to cell death upon exposure to high electric fields when they are in a fully repolarized state, the delivery may be customized to do this as well despite potential arrhythmias that may be generated. Additionally, the pulsed field energy delivery may be timed to occur when asystole is detected after administering adenosine, which may have the transient effect of stopping the heart.

In the third step 74 of the method, the delivery device 12 may be navigated through the patient's vasculature to a target site within the heart. As a non-limiting example, the delivery device may be inserted into the patient's vasculature via femoral access, and may be steered or otherwise passed into the heart and then into the left atrium of the heart, proximate a portion of the atrial wall. Although this step is shown in FIGS. 6 and 7 as coming after the first step of determining the cardiac cycle timing, it will be understood that the device may first be positioned proximate the target site before the patient's cardiac cycle timing is determined.

In the fourth step 76 of the method, the quality of the contact or proximity between the one or more delivery electrodes 18 of the delivery device 12 and the target tissue may be determined. For example, in the method shown in FIG. 6, the fourth step 76 includes evaluating electrode tissue contact and in the method shown in FIG. 7, the fourth step 76 includes evaluating proximity between each electrode 18 and the target tissue to determine which electrodes 18 are in close proximity to, but not in contact with, the target tissue. Any one or more of a plurality of cardiac characteristics may be measured and monitored in this step to help. For example, the quality of electrode-tissue contact may be evaluated based on: (a) intracardiac electrogram (EGM) amplitude; (b) injury current measured using unipolar EGM; (c) EGM morphology whereby the presence of a monophasic action potential (MAP) EGM morphology indicates direct tissue contact, as measured using unipolar EGM; (d) the ability of bipolar or unipolar pacing pulses to achieve cardiac capture through local myocardial stimulation; (e) the amplitude threshold of bipolar or unipolar pacing pulses to achieve cardiac capture through local myocardial stimulation; (f) the proximity to nerves or muscles that may be stimulated by energy delivery, as determined by monitoring responses to stimuli delivered from the delivery electrodes (pacing and sensing may be accomplished with the same electrode); (g) electrode-tissue contact force measurements; (h) temperature response to low-level energy sufficient to produce measurable heating in contacted tissues; (i) low-frequency impedance magnitude measurements; (j) high-frequency impedance magnitude measurements; (k) high-frequency impedance phase angle measurements; (l) current measured during pulsed energy delivery (for example, current delivered during PFA may correspond to electrode-tissue contact, so a higher amount of delivered current may correlate to better contact); (m) the location of each of the one or more delivery electrodes in real time, based on electric potential measurements to determine the 3D position in the heart; (n) the location of each of the one or more delivery electrodes in real time, based on electromagnetic navigation measurements to determine the 3D position in the heart; (o) the location of each of the one or more delivery electrodes in real time, based on electromagnetic or electric field navigation in relation to anatomical sites identified by body surface mapping to be target sites for ablation to treat arrhythmias; (p) the location of each of the one or more delivery electrodes in real time, based on electromagnetic or electric field navigation in relation to anatomical sites identified by non-contact intracardiac sensing or multi-electrode intracardiac endocardial mapping to be target sites for ablation to treat arrhythmias; (q) the location of each of the one or more delivery electrodes in real time, based on ultrasonic transmitting and receiving elements in, for example, the first delivery device 12A and similar ultrasonic transmitting, receiving, or echogenic elements in the second delivery device 12B or secondary device in relation to anatomical sites identified by non-contact intracardiac sensing or multi-electrode intracardiac endocardial mapping to be target sites for ablation to treat arrhythmias; (r) the location of each of the one or more delivery electrodes in real time, based on ultrasound elements incorporated into the electrode array 48 in relation to anatomical sites identified by non-contact or intracardiac sensing or multi-electrode intracardiac endocardial mapping to be target sites for ablation to treat arrhythmia; (s) the instantaneous stability of the one or more delivery electrodes as measured from one or more accelerometers or other sensors 20 mounted in the delivery device; and/or (t) the time in the cardiac cycle and the timing of the respiration cycle as determined by transthoracic and intracardiac impedance measurements (for example, taken from two, three, or four electrodes). All or any of the measurements involved in (a)-(t) may be taken continuously during the PFA procedure.

Such measurements mentioned above may provide information about the contact quality or proximity of the energy delivery catheter and targeted tissue. The measurements indicating tissue contact and/or proximity may be collected from the amplifier system, also known as an EP recording system, where the electrograms from the one or more catheter electrodes are displayed to the operator and may be analyzed, saved, and/or archived. Measurements showing catheter contact and/or proximity may further be collected using a computer-based localization system, also known as an electro-anatomical mapping or navigation system, which may use impedance and/or electromagnetism (contact and/or non-contact) for localization of electrodes and/or catheters. Additionally, measurements may be collected from ultrasound transducers within the energy delivery catheter, as well as from other intracardiac or transthoracic echocardiographic devices used in the procedure, which may provide visual catheter contact and/or proximity information on an echocardiography system. Accelerometers placed in the energy delivery catheter and/or other intracardiac catheters may also provide measurements that provide catheter contact and/or proximity via the voltage associated with the accelerometer movement.

In the fifth step 78 of the method, pulsed phase energy may be delivered from the delivery device 12 to target tissue when the quality of electrode-tissue contact is determined to be adequate (FIG. 6), or the electrodes 18 are located in optimal proximity to the target tissue (FIG. 7), and the contact or proximity occurs at the optimal ablation time within the cardiac cycle. Energy may be delivered such that it causes reversible or irreversible effect on the tissue. For example, the tissue may be stunned (a reversible effect caused) in order to locate a target ablation site and then the site may be ablated (an irreversible effect caused), as discussed above. Timing of the cardiac cycle may be controlled by actively delivering pacing stimuli to the heart just prior to delivery of pulsed field energy. Such pacing may be delivered from, for example, a separate indwelling catheter or from the delivery electrodes 18 of the energy delivery device 12. Once cardiac capture is achieved after a brief series of pacing pulses, for example, capturing the heart for five heartbeats, the energy delivered may be timed to follow the last pacing stimulus within the desired time window and when selected criteria are met that indicate proximity of the energy delivery electrodes 18 to the target tissue. Such energy delivery may be set to a level that stuns the tissue and does not cause substantial irreversible damage or it may be at an irreversible ablative electric field strength. In addition, such energy deliveries may be made, followed by immediate or delayed pacing stimuli that evaluate the effects of the reversible or irreversible energy deliveries.

In addition to or instead of accelerometers, motion or contact with tissue may be detected by other sensors 20 such as piezoelectric elements (such as piezoelectric crystals), strain gauges, or fiber Bragg sensors located in the structure of the electrode array 48 of the one or more delivery devices 12. Such motion, force, or acceleration detectors may be of various designs such as piezoelectric, capacitive, inertial, or optical. Although a generalized sensor 20 is shown in FIGS. 1 and 2, it will be understood that one or more sensors 20 may be used and at locations other than those shown. These sensors 20 may determine relative motions of the electrode array and energy delivery elements of the array, such that energy delivery may be timed to coincide with specific time points whether energy delivery would be on specific tissue sites or more widely distributed tissue sites, as desired by the operator. Optionally, the energy delivery may be distributed over a larger area of tissue to accomplish a larger region of stunning and/or ablation. In such cases, the three-dimensional accelerations, motions, or force/contact detections of the electrode section of a delivery device may be used to determine the extremes of motion within three-dimensional space to deliver energy at the broadest range of locations within an area of the heart or other tissues. Force or wall motion or distension may be used advantageously to lower the threshold at which myocytes death will be achieved. The force or distention may be interpreted as measures of stretch in the tissues with the effect of physically elongating muscle cells to the extent where a lower applied voltage will result in the lethal voltage per myocytes. In such cases, stretched or elongated portions of the heart may be more easily ablated using reduced applied electric field strengths. Especially in such cases of widely distributed energy delivery, it may be desired to use pulsed energy parameters that are optimal for extremely short time frames. In such situations, it may be desired to deliver pulsed energy in pulse durations as short as 0.10 microseconds to up to 20 microseconds. Inter-pulse or inter-phase timing may be set to allow the entire delivery to be completed in a matter of tens of milliseconds or less, depending on the desired precision of the energy delivery to the targeted tissues. Such short pulse durations may also allow the avoidance of nerve and skeletal muscle stimulation, which stimulation may be undesired. In cases where it is desired to spread the energy delivery over a large region, longer pulse trains may be used that extend for many tens of milliseconds or more.

In some embodiments, bipolar energy may be delivered between one or electrodes 18 of the first delivery device 12A and the second delivery device 12B. In that case, optimal ablation timing may be: (a) at the moment of minimal distance between specific or all delivery electrodes 18 on the first delivery device 12A and specific electrodes 18 or all electrodes 18 on the second delivery device 12B; (b) the tissue contact quality or location within the body that is optimal for ablation of the targeted tissue; (c) if the second delivery device 12B or secondary device is used as a local ground return path and not intended to ablate tissues directly adjacent to the second delivery device 12B, the lack of tissue proximity or lack of electrode-tissue contact of the second delivery device 12B; and/or (d) optimal timing as in (a)-(c), determined using ultrasonic transmitting and receiving elements in the first and second delivery devices 12A, 12B by use of the impedance magnitude between electrodes on the first and second delivery device 12A, 12B, by finding and delivering during the minimum impedance value between one or more electrodes on the first and second delivery device, fluoroscopic imaging, electromagnetic field navigation, electric field navigation, or a combination thereof. In a non-limiting example, the first delivery device 12A may be a multi-electrode intracardiac catheter and the second delivery device 12B may be a coronary sinus multi-electrode catheter, and the energy delivery may be selected to be vectored between selected electrodes 18 on the second delivery device 12B and electrodes 18 on the first delivery device 12A determined to be in closest proximity to the chosen one or more electrodes 18 on the second delivery device 12B, based, for example, on location determined using methods (a)-(t) discussed above. Energy delivery may then be delivered between those optimal electrodes on the first and second delivery devices 12A, 12B.

In PFA, tens of milliseconds are a short enough period of time to ensure that the one or more electrodes 18 remain for a long enough period of time in the optimal location to achieve effective energy delivery. In addition to timing the energy delivery to coincide with optimal location and stability of the electrodes in relation to the target ablation site, the energy delivery may also be timed to coincide with the most vulnerable state of the cells within the targeted tissue site. For pulsed field energy delivery, this may include the state of maximum length of the cardiomyocytes or other myocytes. Additionally, there may be vulnerable tissues near the energy delivery electrodes that are not intended ablation targets and should be protected from ablation. In that case, the energy delivery may be timed to coincide with the least vulnerable state of these tissues. This could involve the physical state of the cells within the non-target tissues or it may relate to the moment of least effective energy vectoring to ensure preservation of the non-target tissues. For example, this may be accomplished by activating or deactivating specific electrodes within multi-electrode ablation systems. As a further measure of ensuring no unintended tissue damage occurs, tissue temperature may be measured by a temperature sensor 20A in each electrode 18 immediately after PFA to confirm that no excessive thermal effects were produced.

Further, to enhance the effectiveness of the pulsed field ablation energy in certain cases, it may be desired to create more extensively ablated regions. In such cases, the optimal timing of pulsed field delivery may be at multiple time points in the cardiac cycle. By delivering pulsed fields at more than one or multiple time points in the cardiac motion cycle, the effect of PFA may be more broadly distributed over a tissue surface. This may in turn result in a larger area of ablated myocardium. Such timing of multiple deliveries may be timed to coincide with a range of physical points in space attained during cardiac or respiratory or other patient body motion. The deliveries may be timed to coincide with the extremes of cardiac motion in each of the x, y, and z planes. Such deliveries may also be blanked or prevented from occurring during vulnerable periods of repolarization of the atrial or ventricular myocardium.

Using this method, energy delivery may be avoided during time periods determined to be likely to produce unintended ablation or non-target tissue ablation. In addition to making one or more of the continuous measurements (a)-(t) discussed above, the method may also include monitoring activity over time to determine trends in respiratory, cardiac, or other characteristic cycle lengths. These trends may be evaluated over a period of a few seconds to tens of seconds to verify if changes in position or contact are occurring over time or if the contact and positions of electrodes are stable. Additionally, the relative positions of the electrodes 18 may be monitored in relation to the target sites identified by body surface or other non-invasive mapping techniques to be in adequate proximity to the target sites for energy delivery to achieve the intended ablative effects.

PFA with timed energy delivery may treat most arrhythmias while requiring no more than a few seconds at each tissue site for completion of multiple therapeutic pulsed energy trains while thermal ablation technologies often require between 30 and 240 seconds per energy delivery site. Over the course of a procedure that requires the ablation of multiple sites, PFA can substantially reduce the overall procedure time.

Additionally, PFA techniques may reduce procedure complexity and may eliminate the most feared risks and complications associated with thermal ablation techniques. Also, PFA does not require saline irrigation to cool the electrodes, which eliminates the problem of fluid overload in patients with heart failure or renal complications. Thermal ablation techniques such as radiofrequency ablation may also disrupt the cardiac endothelial surface, active the extrinsic coagulation cascade, and lead to char/coagulum and thrombus formation, which in turn may lead to a risk of systemic thromboembolism, cerebral lesions, and possibly stroke or myocardial ischemia. PFA may also provide important advantages for the treatment of persistent forms of atrial fibrillation (AF). Current treatments for persistent forms of AF include pulmonary vein isolation, which can be done relatively safely with conventional technologies. However, to effectively treat persistent AF, additional ablations are often created in the posterior left atrium, where there is a substantially risk of damaging the esophagus that can be located only millimeters behind the posterior wall. This risk limits the extent to which physicians are willing to ablate, which in turn limits the efficacy of the procedure. Parameters that avoid risks associated with the generation of tissue heating include square wave pulse durations of less than approximately 60 microseconds, for example, less than 20 microseconds. Timing between pulses may range between, for example, 100 and 800 microseconds. Trains of, for example, 10 to 2000 pulses may be used, depending on the specific condition being treated and the desired effect. Effectiveness of energy deliveries may also be enhanced by delivering more than one pulse train in each electrode positioning. This enhancement may be accomplished in cardiac tissues by delivering several pulse trains, with one pulse train being delivered per cardiac cycle.

It will be appreciated by persons skilled in the art that the present application is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

What is claimed is:

1. A method of treating target tissue of a patient's heart with pulsed field energy, the heart having a cardiac cycle, the method comprising:
    positioning a medical device adjacent to the target tissue, the medical device being in communication with a control unit having a pulsed field energy delivery generator;
    determining timing of the cardiac cycle and an optimal time within the cardiac cycle for pulsed field energy delivery;
    evaluating proximity between at least one energy delivery electrode and the target tissue to determine which of the at least one energy delivery electrode is in close proximity with, but not in contact with, the target tissue; and
    delivering pulsed field energy to the target tissue during the optimal time within the cardiac cycle for pulsed field energy delivery from any of the at least one energy delivery electrode that is determined to be in proximity with the target tissue.

2. The method of claim 1, wherein the cardiac cycle timing is determined using body surface electrocardiograms.

3. The method of claim 1, wherein the cardiac cycle timing is determined using intracardiac electrograms.

4. The method of claim 1, wherein the heart includes a ventricle, determining the optimal time within the cardiac cycle for pulsed field energy delivery including identifying depolarization of the ventricle and repolarization of ventricle within the cardiac cycle.

5. The method of claim 4, wherein pulsed field energy is delivered to the target tissue after depolarization of the ventricle and before repolarization of the ventricle.

6. The method of claim 1, wherein determining the cardiac cycle timing includes measuring a QT interval, the QT interval including an R wave, an S wave, and a T wave, and determining the optimal time within the cardiac cycle for pulsed field energy delivery includes identifying an ST segment within the QT interval.

7. The method of claim 6, wherein pulsed field energy is delivered during the ST segment.

8. The method of claim 6, wherein pulsed field energy delivery to the target tissue is initiated approximately 60-120 milliseconds after an onset of the R wave and pulsed field energy delivery is terminated before an onset of the T wave.

9. The method of claim 1, wherein delivering pulsed field energy to the target tissue includes delivering pulsed field energy that causes reversible effects in the target tissue.

10. The method of claim 9, wherein the pulsed field energy delivered to the target tissue is at most approximately 200 V and is delivered in one to 20 pulses.

11. The method of claim 1, wherein delivering pulsed field energy to the target tissue includes delivering pulsed field energy that causes irreversible effects in the target tissue.

12. The method of claim 11, wherein the pulsed field energy delivered to the target tissue is at least approximately 300 V and is delivered in at least one to 20 pulses.

13. The method of claim 1, wherein the evaluation of proximity between the at least one energy delivery electrode and the target tissue is based on at least one of:
    intracardiac electrogram amplitude measured in the target tissue;
    unipolar electrograms measured in the target tissue;
    a presence of a monophasic action potential measured using unipolar electrograms measured in the target tissue, the presence of a monophasic action potential indicating direct contact between the at least one energy delivery electrode and the target tissue;
    an ability of bipolar or unipolar pacing pulses delivered by the at least one energy delivery electrode to achieve cardiac capture through local myocardial stimulation within the target tissue, achieving cardiac capture indicating contact between the at least one energy delivery electrode and the target tissue;
    an amplitude threshold of bipolar or unipolar pacing pulses delivered by the at least one energy delivery electrode to achieve cardiac capture through local myocardial stimulation within the target tissue;
    responses of nerve or muscle tissue proximate the target tissue to energy stimuli delivered by the at least one energy delivery electrode;
    electrode-tissue contact force measurements;
    temperature response to low-level energy sufficient to produce measurable heating in contacted target tissue;
    low-frequency impedance magnitude measurements;
    high-frequency impedance magnitude measurements;
    high-frequency impedance phase angle measurements;
    current measured during pulsed field energy delivery;
    an instantaneous stability of the at least one energy delivery electrode as measured from at least one accelerometer in an energy delivery device; and
    a location of each of the at least one energy delivery electrode in real time, based on at least one of:
        electric potential measurements to determine a 3D location of the at least one energy delivery electrode within the heart;
        electromagnetic navigation measurement to determine a 3D position of the at least one energy delivery electrode within the heart;
        electromagnetic or electric field navigation in relation to anatomical sites identified by body surface mapping to be target sites for energy delivery to treat arrhythmias;
        electromagnetic or electric field navigation in relation to anatomical sites identified by non-contact intracardiac sensing or multi-electrode intracardiac endocardial mapping to be target sites for energy delivery to treat arrhythmias;

ultrasonic transmitting and receiving elements of a first medical device and ultrasonic transmitting, receiving, or echogenic elements in a second medical device in relation to anatomical sites identified by non-contact intracardiac sensing or multi-electrode intracardiac endocardial mapping to be target sites for energy delivery to treat arrhythmias; and ultrasound elements incorporated into a treatment device in relation to anatomic sites identified by non-contact or intracardiac sensing or multi-electrode intracardiac endocardial mapping to be target sites for energy delivery to treat arrhythmias.

14. The method of claim 1, wherein each of the at least one energy delivery electrodes includes at least one temperature sensor, the evaluation of contact between the at least one energy delivery electrode and the target tissue being based on a temperature measurement recorded by the at least one temperature sensor immediately following the delivery of pulsed field energy.

* * * * *